(12) United States Patent
Theuer et al.

(10) Patent No.: US 11,752,365 B2
(45) Date of Patent: Sep. 12, 2023

(54) DEVICE FOR TREATING MALIGNANT DISEASES WITH THE HELP OF TUMOR-DESTRUCTIVE MECHANICAL PULSES (TMI)

(71) Applicants: Axel Erich Theuer, Kirchberg (DE); Irmengard Theuer, Kirchberg (DE)

(72) Inventors: Axel Erich Theuer, Kirchberg (DE); Irmengard Theuer, Kirchberg (DE)

(73) Assignees: Irmengard Theuer, Kirchberg (DE); Axel Erich Theuer, Kirchberg (DE)

( * ) Notice: Subject to any disclaimer, the term of this patent is extended or adjusted under 35 U.S.C. 154(b) by 1099 days.

(21) Appl. No.: 16/473,923

(22) PCT Filed: Dec. 28, 2016

(86) PCT No.: PCT/EP2016/082793
§ 371 (c)(1),
(2) Date: Oct. 10, 2019

(87) PCT Pub. No.: WO2017/137134
PCT Pub. Date: Aug. 17, 2017

(65) Prior Publication Data
US 2020/0038694 A1 Feb. 6, 2020

(30) Foreign Application Priority Data

Feb. 9, 2016 (DE) .................... 10 2016 001 409.1
Apr. 19, 2016 (DE) .................... 10 2016 004 616.3

(51) Int. Cl.
*A61N 7/02* (2006.01)
*A61B 8/08* (2006.01)
(Continued)

(52) U.S. Cl.
CPC .............. *A61N 7/02* (2013.01); *A61B 8/0808* (2013.01); *A61B 8/0825* (2013.01); *A61B 8/14* (2013.01);
(Continued)

(58) Field of Classification Search
CPC ...... A61N 7/02; A61B 8/0808; A61B 8/0825; A61B 8/14; A61B 17/22022; A61B 2017/22025
See application file for complete search history.

(56) References Cited

U.S. PATENT DOCUMENTS 6,334,846 B1 * 1/2002 Ishibashi ................ A61B 5/055
600/439
8,932,237 B2 * 1/2015 Vitek ....................... A61N 7/02
601/2
(Continued)

FOREIGN PATENT DOCUMENTS

DE 4414239 A1 * 10/1994 ............ A61N 7/00
DE 4414239 A1 10/1994
(Continued)

OTHER PUBLICATIONS

Bozec, L., et al., "Thermal Denaturation Studies of Collagen by Microthermal Analysis and Atomic Force Microscopy," Biophysical Journal. vol. 101, 2011. p. 228-236 (Year: 2011).*

*Primary Examiner* — Keith M Raymond
*Assistant Examiner* — Sean A Frith
(74) *Attorney, Agent, or Firm* — Volpe Koenig

(57) ABSTRACT

A device and a method, which is individual to a patient, treat malignant diseases by using selectively acting tumor-destructive mechanical pulses (TMI). The tumor-destructive pulse shapes are determined using physical cell properties, which are individual to each patient. The device is controlled in such that lethal pulse fields are applied in the tumor area.

23 Claims, 15 Drawing Sheets

(51) Int. Cl.
*A61B 8/14* (2006.01)
*A61B 17/22* (2006.01)

(52) U.S. Cl.
CPC ............... *A61B 17/22022* (2013.01); *A61B 2017/22025* (2013.01)

(56) References Cited

U.S. PATENT DOCUMENTS

| | | | |
|---|---|---|---|
| 9,248,318 B2 * | 2/2016 | Darlington | A61N 7/02 |
| 2008/0146971 A1 * | 6/2008 | Uebelacker | A61B 17/22004 |
| | | | 601/4 |
| 2010/0081857 A1 * | 4/2010 | Georgi | A61K 51/1045 |
| | | | 600/1 |
| 2010/0092424 A1 * | 4/2010 | Sanghvi | A61B 8/0833 |
| | | | 424/85.2 |
| 2011/0034209 A1 * | 2/2011 | Rubinsky | G16H 40/67 |
| | | | 455/556.1 |
| 2011/0251528 A1 * | 10/2011 | Canney | A61N 7/02 |
| | | | 601/3 |
| 2011/0270139 A1 * | 11/2011 | Bauer | A61B 17/00 |
| | | | 601/4 |
| 2012/0109024 A1 * | 5/2012 | Theuer | A61B 8/406 |
| | | | 601/3 |
| 2013/0058195 A1 * | 3/2013 | Cloutier | A61B 8/085 |
| | | | 367/99 |
| 2014/0107540 A1 * | 4/2014 | Murakami | A61N 7/022 |
| | | | 601/3 |
| 2014/0257144 A1 * | 9/2014 | Capelli | G10K 11/26 |
| | | | 601/2 |
| 2015/0209551 A1 * | 7/2015 | Burdette | A61B 5/055 |
| | | | 600/411 |
| 2016/0022976 A1 * | 1/2016 | Peyman | A61B 5/0036 |
| | | | 600/439 |
| 2017/0071515 A1 * | 3/2017 | Chevillet | A61B 10/007 |

FOREIGN PATENT DOCUMENTS

| | | | | |
|---|---|---|---|---|
| DE | 10302438 A1 * | 7/2004 | | A61N 7/00 |
| DE | 10302438 A1 | 7/2004 | | |
| DE | 102016111727 A1 | 12/2016 | | |
| WO | 2001037735 A2 | 5/2001 | | |
| WO | 2009156156 A1 | 12/2009 | | |
| WO | 2010020406 A1 | 2/2010 | | |
| WO | 2010049176 A1 | 5/2010 | | |

* cited by examiner animal No 042

| lenght$_a$ (mm) | width$_a$ (mm) | thickness$_{aH}$ (mm) | volume (mm³) |
|---|---|---|---|
| \multicolumn{4}{c}{ESWT} | | | |

| lenght$_a$ (mm) | width$_a$ (mm) | thickness$_{aH}$ (mm) | volume (mm³) |
|---|---|---|---|
| 7 | 7 | 3 | 72 |
| 11 | 9 | 4 | 191 |
| 14 | 14 | 7 | 718 |
| 18 | 14 | 12 | 2111 |
| 19 | 17 | 12 | 2432 |
| 19 | 18 | 12 | 2518 |
| 20 | 18 | 12 | 2606 |
| 21 | 19 | 13 | 3192 |
| 20 | 18 | 9 | 1658 |
| 20 | 18 | 8 | 1402 |
| 22 | 18 | 7 | 1279 |
| 22 | 18 | 9 | 1795 |
| 22 | 19 | 7 | 1335 |
| 20 | 17 | 5 | 737 | animal No 063

| ESWT + Nivoliumab | | | |
|---|---|---|---|
| lenght$_a$ (mm) | width$_a$ (mm) | thickness$_a$ (mm) | volume (mm$^3$) |
| 10 | 10 | 3 | 132 |
| 14 | 12 | 4 | 299 |
| 16 | 14 | 9 | 1177 |
| 21 | 16 | 11 | 2175 |
| 20 | 17 | 13 | 2898 |
| 19 | 18 | 12 | 2518 |
| 20 | 17 | 6 | 920 |
| 20 | 19 | 5 | 812 |
| 20 | 18 | 6 | 964 |
| 21 | 17 | 7 | 1172 |
| 21 | 17 | 3 | 439 |

DEVICE FOR TREATING MALIGNANT DISEASES WITH THE HELP OF TUMOR-DESTRUCTIVE MECHANICAL PULSES (TMI)

CROSS REFERENCE TO RELATED APPLICATIONS

This application is a United States National Phase Application of International Application PCT/EP2016/082793, filed Dec. 28, 2016, the entire contents of which are incorporated herein by reference.

TECHNICAL FIELD

The invention relates to a device for treating malignant diseases with the help of tumor-destructive mechanical impulses (TMI) and defines the operation and the control of this device.

TECHNICAL BACKGROUND

Devices for the treatment of diseased cells in living bodies by way of sound and/or ultrasound waves have already been known for several decades. Hence a device is described in DE 44 14 239 A1, concerning which a sound source is designed for the selective destruction of cells of diseased appearance, for example tumor cells, for the production of sound waves and/or ultrasound waves with a resonance frequency spectrum which is typical for the respective cell type and which destroys these cells.

An arrangement for the destruction of tumor cells is known from WO 2009/156156 A1, concerning which an ultrasound generator for producing a thermally effective, high-frequency oscillation comprises several low-frequency ultrasound generators which each produce a different frequency, and a control which is connected to a high-frequency ultrasound generator so that the tumor cells can be subjected to a high-frequency oscillation which thermally acts upon the tumor cells, and to a low-frequency oscillation, wherein a biopsy device with several individual receivers for tissue samples is provided.

A device for destroying tumor cells or germs in the blood circulation is known from WO 2010/020406 A1, concerning which the at least one ultrasound frequency generator and a device for forming an extracorporeal blood circulation are provided, wherein the device comprises at least one heat exchanger, a blood delivery pump and a treatment container for receiving blood, wherein the treatment container is arranged subsequently to the heat exchanger, forms a treatment space and is connected to at least one ultrasound oscillation head. The ultrasound oscillation head is coupled to the ultrasound frequency generator, so that a low-frequency ultrasound oscillation can be introduced into the treatment space.

A medical device for treating tumor tissue is known from WO 2010/049 176 A1, said device comprising a surgical instrument which can be introduced into a body and which is with a housing, in which an oscillation element which can be actuated for producing an ultrasound oscillation is arranged. A transmission region which at least partly comprises a wall of the housing which on use is arranged facing the tumor tissue to be treated is assigned to the oscillation element. The transmission region, on use, is adapted to transmit the ultrasound oscillation into the tumor tissue which is to be treated. The transmission region interacts with at least one temperature control device.

A device for the oscillation-induced, selective treatment of malignant diseases with the help of mechanical oscillations and/or sound waves, concerning which by way of a targeted selection it is those cells which are to be treated with the help of the device which are affected, is known from WO 2001/37735 A1. A microsurgical device which comprises an oscillation generator is provided for this.

SUMMARY

It is an object of the invention to specify a tumor-destructive mechanical impulse (TMI) device for the treatment of malignant diseases with the help of mechanical impulses and to define the operation and control of the device, which achieves a further improvement of the treatment compared to the devices and methods known from the state of the art, as well as can be expanded to other forms of therapy.

A device according to the invention (TMI) device, for the treatment of malignant diseases with the help of tumor-destructive mechanical impulses, uses a cell-biologically optimized, optically destructive, tumor-selective patient individual impulse shape and/or impulse sequences, said impulse shape and/or impulse sequences resulting from or being adapted to the mechanical, more viscoelastic characteristics of the tumor cells and the extracellular matrix (ECM) which is intra-tumoral or encompasses the tumor.

A method according to the invention, for the operation and the control of the TMI device comprises an optimal impulse shape and/or impulse sequence and/or further operating parameters being determined in a cell trial of cells which are taken from a patient or by way of a tissue trial or being taken from a data bank for cell trials and tissue trials, before the application of the device, wherein physical characteristics of the removed cells are determined via measurements, in particular AFM (atomic force microscopy) measurements and are integrated into FEM (finite element) simulation models.

The device can be configured for applying a cell-biologically optimized, optimally destructive and tumor-selective pressure shock impulse sequence.

Furthermore, a cell-biologically optimized, optimally destructive and tumor-selective delay time can be adjusted or be adjustable between the impulses.

One can envisage the device being configured by way of expanding a target volume which is to be subjected to impulses, into healthy tissue, for destroying tumor-active fibroblasts.

The device can comprise at least one pressure sound head and at least one control unit for activating the pressure sound head for producing the tumor-destructive mechanical impulses or impulse sequences.

It can further comprise at least one positioning mechanism for positioning the pressure sound head relative to a target volume which is subjected to the impulses, preferably in accordance with the control unit.

One can envisage the pressure sound head being positioned or positionable and being modulated or and/or modulatable with regard to its impulse delivery, in a manner such that tumor-destructive shear forces arise in the target volume.

One can also envisage at least two pressure sound heads or oppositely polarised piezoelements being provided in a phased array technology, preferably with suitable positioning mechanisms, for the generation of the tumor-selective impulse shapes and impulse sequences.

Moreover, one can envisage providing at least three or more pressure sound heads with corresponding positioning mechanisms, in particular for the treatment of mammary carcinoma or brain metastases, wherein preferably the pressure sound heads are positioned or positionable and with regard to their impulse delivery are modulated or modulatable, in a manner such that tumor-destructive shear forces arise in the tumor region.

The positioning mechanisms can be controlled or controllable such that a preferably point-like focus region is firstly directed onto the tumor edge and scans this, wherein the impulse flanks preferably comprise high-frequency components of about 1 MHz to 10 MHz due to the high-frequency, tumor-protective TAF (cancer associated fibroblasts) on the tumor edge.

The positioning mechanisms can further be controlled in a manner such that a preferably point-shaped focus region is directed onto the target volume and scans this, wherein impulse flanks comprise patient-individual, low frequency components, preferably at about 0.1 MHz-3 MHz.

The device can be configured to heat a target volume to about 39° C. to 41° C., preferably to about 40° C., by way of suitable impulse or impulse sequences, in order to further improve its effectiveness.

The device can comprise at least one ballistic and/or at least one electrohydraulic or piezoelectric shockwave generator or corresponding treatment applicators, in particular for producing positive shockwave impulses.

The at least one ballistic shockwave generator can be provided for producing second shockwave impulses with defined, tumor-destructive characteristics.

The device can comprise at least two shockwave generators and a control unit, wherein the shockwave generators are successively activated or activatable by the control unit in a manner such that the respective pressure maxima of the shockwave impulses are successive in a temporal interval which is smaller than the impulse duration of the shockwave impulse.

Furthermore, the device can be provided with at least one diagnostic unit for the continuous monitoring of a treatment success, in particular for monitoring an ultrasound echo image (frequency spectrum) of a tumor region, a number of circulating tumor cells in the blood and/or immune parameters.

A further development of the method envisages the operating parameters being determined in a patient-individual manner with the help of physical characteristics of cells which are taken from a patient and are determined on the basis of MRT/CT data of the patient.

Another further development of the invention envisages lethal impulse shapes and impulse sequences being determined and experimentally validated with the help of patient-individual numerical simulation models.

Yet another further development of the invention envisages the operation of the TMI treatment being effected via a central treatment center (CTC) and decentral treatment facilities (TF).

The TMI device can also be aligned to tumor-affected lymph nodes which can herewith be individually treated and do need to be excised.

The TMI device can be simultaneously applied with the application of immunomodulators.

In a preferred embodiment, the TMI device comprises treatment applicators or pressure sound heads which serve for the application of mechanical impulses or shockwaves. The treatment applicators preferably further have a possibly decentrally arranged diagnostic unit. Ultrasound echo waves can therefore be evaluated between treatment pulses and short impulses in the low intensity region can be emitted for exciting and evaluating the pulse-echo (spectral analysis).

The TMI device can further comprise an impulse generator or several impulse generators. Herein, depending on the application purpose, ultrasound generators or shockwave generators are applied, concerning which the mechanical impulses are produced ballistically, piezoelectrically, electromechanically or electro-hydraulically. In case of several shockwave generators or impulse generators, it can be useful if different shockwave generators are present, for example one operating in a ballistic manner and one in an electro-hydraulic manner.

Piezoelectric impulse generators are fashioned in a planar or focused manner in accordance with the tumor type and the position of the tumor region. Herein, tumor-destructive impulse fields can be effected with the help of a sequence of capacitive discharges or with the help of tumor-specific pulsed sinusoidal oscillations in the high intensity range (60.0-200.0 Mpa).

It is advantageous if the components of the treatment applicators, apart from focused, electromagnetic or piezoelectric impulse generators, comprise low-frequency (20-30 kHz) plane impulse generators, a diagnostic unit, positioning mechanism and a transmission medium.

The focused impulse generators can produce preferably continuous or pulsed high-intensity sine oscillations which apply pressure shock impulses in the focus region due to the steepening of the sine wave, or low intensity pulsed sinusoidal oscillations which induce resonance phenomena in the tumor region. Herein, it is advantageous to vary the power of the TMI impulse generators, in order to be able to apply sequentially steepened pressure shock impulses and continuous sinusoidal oscillations.

A coupling surface which can be applied for example onto a body region of a patient who is to be treated is preferably present for introducing the produced impulse fields. The coupling surface can be e.g. a cavity of the treatment applicator which is filled with a transmission fluid. Concerning a ballistic shockwave generator, an impact plate which preferably consists of metal and onto which a projectile is shot is present, wherein the side of the impact plate which is away from the shooting direction of the projectile forms the coupling surface (however, further intermediate elements can be present).

As a further component or as a further constituent, in a preferred embodiment the device comprises a control unit which is signal-connected to the at least one impulse generator. If here, one speaks simply speaks of control unit, then this is also to be understood as a unit which is suitable for controlling or regulating (closed-loop controlling). Herein, the control unit can be configured such that the impulse generators produce impulses with an impulse frequency of 0.5 Hz to 600 Hz, with a maximal pressure in an absolute value of 0.01 MPa to 300 MPa and with a ascent time of 2 ns to 4000 ns, without the invention being restricted to these values.

Tumor cells, in particular also therapy-resistant tumor cells such as those which are resistant to Vermurafenib, a protein kinase blocker, can be destroyed with such a TMI device in a selective manner, i.e. without damage or with only little damage to the healthy tissue or healthy cells, by way of necrosis and/or by way of initiating apoptotic processes. Herein, for the tumor-destructive effect it is particularly essential for the impulse frequency and the impulse sequence to be adapted to the respective tumor type in accordance with invention and hence to able to produce an effect on the tumor tissue of a cell or cell organelles which are extended by the shockwave which is produced by the TMI device, of being subjected to a subsequent shockwave, before the cell or the cell organelles has/have returned again into their initial state. Healthy body cells are more mechanically stable in comparison to tumor cells and are herein merely deformed in a non-harmful way and manner, whereas tumor cells are permanently destroyed or damaged. The mechanical impulses which are formed by the TMI device can be positive as well as negative or inverted shockwaves, wherein an impulse sequence of shockwaves can comprise both types of pressure waves. Particularly high and destructively acting shear forces can be produced on tumor cells and tumor cell organelles with several modulated shockwaves or pressure waves.

Within the framework of the invention, selective, tumor-destructive impulse shapes and impulse sequences are determined from tumor-specific, more viscoelastic characteristics of malignant cells and from the intratumoral extracellular matrix (ECM) which is to say the extracellular matrix which encompasses the tumor, preferably outside the body and after a suitable biopsy. Tumor cells have pronounced, tumor-specific mechanical characteristics. Viscoelastic characteristics of malignant protein structures are of particular relevance. The stiffness of cells is primarily determined by the cytoskeleton and the size and consistency of the cell organelles. The cytoskeleton consists of a multitude of different protein structures and determines the total stiffness of the cell. It is particularly actin filaments, microtubules, microfilaments and interfilaments which gives rise to the cellular total stiffness and determine the mechanical characteristics and the dynamic behaviour of cellular structures. Actin filaments and microtubules play a particularly important role. Actin filaments determine the dynamic deformation behaviour of the cells. They support the cell membranes. With regard to most malignant cells, particularly on the cortical inner side, actin filaments are almost not present at all, are less bundled and cannot fulfil their physiological, protective support function of malignant cell membranes.

Our own computations and validating cell trials, tissue trials and animal trials have led to the recognition that specific, selectively acting tumor-destructive impulses have the capability of selectively necrotically destroying tumor cells and tumor tissue and even have a tumor-destructive effect with therapy-resistant cells (for example Vermurafenib). Healthy cells survive the impulse sequence without damage.

The physical characteristics (stiffness, viscosity, density, size and kinematic solidification) of tumor cells of one patient differ from the physical characteristics of a second patient. In this context, one speaks of patient-individual physical characteristics of tumor cells.

Deformations of the cells and of the cell organelles occur on propagation of the impulse fields which are produced by way of the TMI device, through the tumor region. If the value of the membrane extensions (particularly in the tangential region) exceeds a lethal value, a necrotic failure occurs. The cell membrane tears and malignant protein structures flow into the surrounding ECM. Malignant cell fragments, malignant protein structures and particularly mitochondrial fragments are expelled. Herein, a tumor-specific maturation of dendritic cells can occur. These present tumor-toxic characteristics to native T-cells and can lead to an advantageous tumor-toxic response of the immune system.

Healthy cells survive the tumor-specific impulse fields without any damage, since they have an intact actin filament. The stiff cortical actin filament of healthy, non-degenerate cells supports the membranes of healthy cells and has a membrane-protective effect for these.

The invention describes tumor-specific impulses and tumor-specific impulse sequences. Impulse sequences are determined by the impulse frequency and the number of impulses. What is of relevance to the invention is the viscoelastic delay behaviour of malignant cell structures. After the occurrence of the first impulse or impulse fields, significant extensions occur in malignant cells. These are more pronounced than in normal cells. The second, temporally successive impulse fields amplify the already built-up extension fields. As a result, the extensions are built up further until reaching lethal values and lead to lethal damage in malignant cells and cell organelles.

Healthy, non-degenerate cells—as has already been explained—are significantly stiffer than malignant cells and require longer time intervals, in order to reach lethal extensions. With short impulse sequences, they remain below critical, cell-destructive values and survive the treatment without damage.

With a suitable further development of the invention, selectively acting impulse fields which destroy mitochondria are particularly advantageous.

The mitochondria of malignant cells are significantly more sensitive to pressure compared to mitochondria of healthy cells. They are embedded in an unbundled, relatively soft actin filament. They are torn by way of the applied impulses and impulse sequences and effect the release of cytochrome. Cytochrome c binds to the APAF-1 protein which oligomerises and activates the initiator caspase 9 and subsequently the effector caspase 3. These are the so-called death receptors which lead to an apoptotic failure of the tumor cells.

With ultra-short impulses (ascent times of <10 ns) in the focus region and which can be applied given a suitable design of the invention, the mass inertia of the cells and the cell organelles is too large to build up lethal extensions fields. The cells and cell organelles cannot follow the impulse front and are retained as a whole. However, on the mitochondrial level, the impulse front firstly hits the mitochondrial outer membranes. With ultra-short impulses, the opposed mitochondrial membrane is not burdened at the time of this hitting. Herewith, mitochondrial membranes are subjected to extreme pressure differences. They effect complex mitochondrial signal cascades and the triggering of free radicals (NO and hydroxyl OH). A significant role is played by these as signal and modulators on forming heat shock proteins. Apoptotic processes are triggered in malignant cells.

A further aspect of the device which is of relevance to the invention is the concomitant or time-shifted treatment of cancer associated fibroblasts (CAFs). CAFs are life-important preconditions for the mitoses and metastasis of malignant cells. A significant role is given to them on inactivating the immune system in the tumor region. For this reason, it is absolutely necessary to completely destroy activated fibroblasts in the tumor region. For this purpose, given a suitable embodiment of the invention, specific impulse fields are applied concomitantly or a time staggered manner for the selective destruction of cancer associated fibroblasts (CAFs) in the tumor region. CAF-specific impulse fields can be determined in prior FEM analyses. The selectivity is given by CAF-specific material characteristics and the spindle-shape of cancer associated fibroblasts. These material characteristics of CAFs can be determined with the help of AFM measurements.

Likewise of relevance to the invention is the activation of commercially available photo-sensitisers. It has been surprising found that the tumor-destructive impulse fields which are used with a suitable design of the invention have the capability of activating photosensitisers. Selectively acting tumor-toxic compounds arise. These, in combination with the applied impulse fields, can effect pronounced tumor-specific response reactions of the immune system.

Our own simulation analyses and validating trials have led to the recognition that tumor-specific impulses also have tumor-destructive characteristics with tumor diseases with a reduced apoptosis rate, such as for example colon carcinoma, pancreatic carcinoma and hepatocellular carcinoma. Our own examinations indicate that special impulses are in the position of selectively destroying tumor stem cells and also tumor stem cells which are resistant to chemotherapy and radiation therapy.

It has been surprising found that TMI (tumor-destructive mechanical impulses) lead to an activation of the immune system. Numerous malignant cell fragments and expelled malignant protein structures via the dendritic cells (D-cells) induce tumor-toxic characteristics to the T-cells of the immune system. A dramatic increase of CD8 T-cells with tumor-toxic characteristics could be ascertained in the blood of TMI-treated, tumor-carrying immunocompetent animals.

Since tumor cells are in the position of successfully repelling TMI induced T-cells with tumor-toxic characteristics, a further development of the present invention preferably comprises a combination of TMI treatment with PD1 inhibitors (e.g. Nivolumab). Herein, PD1 inhibitors are administered concomitantly or after the TMI treatment.

The treatment is carried out until circulating metastasis cells (ZM) can no longer be ascertained in the blood of the patient. Herein, a new acoustic method can be applied, with regard to which ZMs are excited into tumor-specific oscillations by way of short extracorporeal impulses and then acoustically detected.

It is advantageous to realize the invention in the form of a CTC (cancer treatment center) and individual TF (treatment facilities) which are positioned worldwide, and these will be dealt with in more detail hereinafter (cf. FIG. 3).

In this context, given a corresponding further development, the invention can comprise the following distinct steps:
In the TF, tumor cells are taken from the patient on location and are sent to the CTC.
In the CTC, AFM measurements of the patient cells are carried out and the measured physical characteristics are integrated into predefined, stable FEM models. Patient-individual lethal impulse shapes and impulse sequences result.
In a second step, MRT data of the tumor region is transferred from the TF to the CTC and are integrated into predefined, stable FEM models. Patient-individual treatment parameters result and these are transferred to a CPU (central processing unit)) of the relevant TF. The treatment parameters contain patient-individual control impulses and patient-individual position coordinates of the treatment applicators. Herewith, it is ensured that lethal impulse shapes and impulse sequences can be applied in the tumor region.
In a further step, therapy-accompanying diagnostic patient data is transferred to the CTC in a continuous manner and evaluated spectral-analytically. The treatment applicators preferably have a centrally arranged diagnostic unit. Ultrasound echo waves are evaluated between the pulses and short impulses in the low intensity range are emitted for exciting and evaluating the pulse echo (spectral analysis).
It has been surprising found that TMI (tumor-destructive mechanical impulses) lead to an activation of the immune system. Numerous malignant cell fragments and expelled malignant protein structures, via the dendritic cells, induce tumor-toxic characteristics in the T-cells of the immune system. A dramatic increase in CD8 T-cells with tumor-toxic characteristics could be ascertained in the blood of TMI treated, tumor-carrying, immunocompetent animals.
Since metastasis cells, dendritic cells as well as T-cells of the immune system are present in the affected lymph nodes, according to the invention, diagnostic patient data of tumor-affected lymph nodes are sent to the CTC. These are integrated into predefined, stable FEM models and are solved numerically. Patient-individual treatment parameters result, these being sent to the CPU (central control unit) of the TF. The treatment parameters contain patient-individual control impulses of the CPU and patient-individual position coordinates for the treatment of affected lymph nodes.
Since tumor cells are in the position of successful repelling TMI induced T-cells with tumor-toxic characteristics, in the context of the present invention a combination of the TMI treatment with PD1 inhibitors (e.g. Nivolumab) can be effected. Herein, PD1 inhibitors are administered concomitantly or after the TMI treatment.
The treatment is carried out until circulating metastasis cells (ZM) can no longer be ascertained in the blood of the patient. Herein, an acoustic method can be applied, with regard to which the ZMs are excited by the short extracorporeal impulses into tumor-specific oscillations and are acoustically detected.
It is advantageous if the components of the treatment applicators, apart from focused electromagnetic or piezoelectric impulses, comprise low-frequency (20-30 kHz) plane impulse generators, a diagnostic unit, positioning mechanisms and a transmission medium (FIG. 2).
The focused impulse generators can preferably produce continuous or pulsed high intensity sinusoidal oscillations which apply pressure shock impulses in the focus region due to the steepening of the sine wave or low intensity pulsed sinusoidal oscillations which induce resonance phenomena in the tumor region. Herein, it is advantageous to vary the power of the TMI impulse generators, in order to apply sequentially steepened pressure shock impulses and continuous sinusoidal oscillations (FIG. 16).

Likewise of relevance to the invention are specific, tumor-destructive or treatment-specific impulse fields, their temporal variation, modulation, combination, diagnostic accompaniment and control with the help of a preferably software-assistant regulation and control unit.

Viscoelastic FEM simulation models of the cellular structures and tissue regions which are to be treated, are prior to such or accompany such. The input parameters of the FEM simulation analyses are physical characteristics of the cells and cell structures which are to be treated. These preferably result from AFM measurements or electrical measurements of living cells and cell organelles or are taken from an individual CTC data bank.

Our own computations and analyses have further led to the recognition that sickle cells can also be brought into apoptotic processes by TMI therapy. Concerning sickle cell diseases, cell-maintaining, apoptotic processes are of particular importance since a necrotic destruction leads to possible adhesions of the cell fragments and the already more difficult blood circulation is worsened further. Furthermore, ultra-short impulse fields due to the NO release have vasodilatory capabilities which play an eminently important role with sickle cell diseases.

Concluding, it is to be ascertained that specific, patient-individual tumor-destructive mechanical impulses of the TMI device as well as preferably their temporal variation, modulation, combination, diagnostic accompanying and control define the essence of the invention. Patient-specific viscoelastic FEM simulation models of the cellular structures and tissue regions which are to be treated can be prior to this. The input parameters of the FEM simulation analyses are physical characteristics of the cells and cell structures to be treated, and are preferably determined via AFM measurements.

Breast cancer is worldwide the most common invasive tumor disease concerning women. Worldwide there are about 1,050,000 new cases of the disease very year. In Germany there are about 71,000 new cases of the disease per year. The TMI treatment of the mammary carcinoma can comprise the following distinct steps: Firstly AFM measurements of the patient cells are effected for determining the patient-individual physical characteristics. These are integrated into predefined, stable FEM models. Patient-individual lethal impulse shapes and impulse sequences result. In a second step, MRT/CT data of the tumor regions is integrated into predefined, stable FEM models. Patient-individual treatment parameters which are transferred to the CPU (central processing unit) of the TMI device result. The treatment parameters comprise patient-individual control impulses and patient-individual position coordinates for the positioning mechanisms of the treatment applicators for the sequential scanning of the complete tumor region. Herewith, it is ensured that lethal impulse shapes and impulse sequences are applied in the tumor region. Since metastasis cells of the mammary carcinoma, dendritic cells as well as the T-cells of the immune system are present in the affected lymph node of the mammary carcinoma, according to the invention diagnostic MRT/CT patient data of tumor-affected lymph nodes are integrated into predefined, stable FEM models and are numerically solved. Patient-individual treatment parameters result. These comprise patient-individual control impulses and patient-individual position coordinates for TMI treatment of the affected lymph nodes of the mammary carcinoma.

Our own computations and validating cell trials, tissue trials and animal trials have led to the recognition that cells of the mammary carcinoma can be lethally damaged by way of specific, selectively acting tumor-destructive mechanical impulses. Healthy cells survive the treatment without any damage. The cells of metastases of the mammary carcinoma behave for the most part just as the cells of the primary tumor and have the same or very similar mechanical characteristics which determine the therapy.

Our own FEM analyses of the pressure propagation through the breast tissue and accompanying tumor trials have led to the recognition that tumor-destructive pressure peaks can be built up in the affected area. A patient-individual positioning of the treatment applicators is necessary for this. Tumor-destructive impulse shapes and impulse sequences result from the results of the FEM simulation analyses of the pressure propagation.

Prostate cancer is by far the most commonly diagnosed malignant tumor of men. In Germany, about 26.500 men are diagnosed with prostate cancer each year. Prostate cancer is at second place in the statistics concerning organ-related cases of death due to cancer. Again, the TMI device operates by way of mechanical impulse fields and comprises the impulse generators, a control device as well as treatment applicators which however in this application case can have another form. The treatment applicators can be arranged on an anatomically arcuate holding device via the positioning mechanism. Impulses of the treatment applicators are transmitted onto the tumor region. The treatment applicators which are flexibly integrated in the holding device are aligned onto the tumor region and are subjected to tumor-destructive impulse sequences via the control unit. Tumor nodes are treated via several treatment applicators which are focused onto the node. Tissue which surrounds the tumor, with tumor protective fibroblasts (TAFS) which are activated by the tumor are scanned by lethal impulse shapes which are applied in a point-like manner and are treated concomitantly or in a time-shifted manner.

Concerning the TMI device for the treatment of the prostate carcinoma and bone metastases of the prostate carcinoma, affected lymph nodes are also explicitly treated. An essence of the invention is also for affected lymph nodes of the prostate carcinoma to be treated. For this, highly resolved MRT/CT patient data is integrated into predefined stable FEM models. These are solved numerically and the position of the treatment applicators is determined such that the pressure propagation is aligned onto the lymph nodes and lethal impulse shapes and impulse sequences are applied into the lymph node.

The TMI device can also comprise several different impulse generators for the treatment of the prostate carcinoma. Herein, it can be useful to apply piezoelectric, ballistic or electromagnetic impulse generators or a combination of the mentioned impulse generators. With regard to the extracorporeal treatment of the prostate carcinoma, the provision of two electromagnetic treatment applicators BA is preferred from an organ-specific point of view. These can be operated synchronously or asynchronously.

The TMI device for the treatment of bone metastases of the prostate carcinoma is preferably characterised by low-frequency treatment applicators (30 kHz-800 kHz) which operate in the high intensity range (20.0 MPA-200 MPA). Since tumor regions of bone metastases are predominantly positioned on the inner side of the greatly absorbing compacts, impulse shapes with low-frequency components in the frequency spectrum and the afore-described treatment parameters are necessary, in order to overcome the greatly absorbing compacta of the affected bone structures.

Moreover, tissue trials and animal trials have led to the recognition that bone metastasis cells can also be lethally damaged by specific, selectively acting tumor-destructive mechanical impulses. Healthy cells survive the treatment without damage.

The cells of bone metastases behave for the most part as the cells of the primary tumor and have the same or very similar mechanical characteristics which determine the therapy.

According to the invention, the physical characteristics of patient-individual metastasis cells are determined via AFM (atomic force microscopy) before the TMI treatment of bone metastases, are integrated into FEM simulation models of non-linear pressure propagation through the tumor region and treatment parameters which lead to the lethal damage of malignant cells in the tumor region are determined with the help of comparative comparisons of the simulation results.

Patient-individual prostate carcinoma cells are taken from the regions of the tumor or circulating metastasis cells are separated from the blood of the patient, and therapy-determining physical characteristics are determined with the help of AFM measurements.

Our own FEM analyses of the pressure propagation through bone structures and accompanying tumor trials have led to the recognition than tumor-destructive pressure peaks can be built up in the affected bone marrow. For this, a patient-individual positioning of the treatment applicators is necessary. Tumor-destructive impulse shapes and impulse sequences result from the results of the FEM simulation analyses of the pressure propagation through absorbing bone structures. Herein, tumor-destructive impulse fields can be produced with the help of capacitive discharges or with the help of pulsed sine oscillations.

Furthermore, ballistic treatment applicators, piezoelectric treatment applicators or also a combined construction of ballistic treatment applicators and piezoelectric treatment applicators can be applied.

The applicant has recognized that selective, tumor-specific impulse shapes can be used for different tumor identities. The selectivity of tumor-destructive impulse shapes result from the mechanical, more viscoelastic characteristics of the tumor cells and the extracellular matrix (ECM) which is intertumoral which is to say encompasses the tumor. An extension of the cell membranes and cell organelles occurs with the propagation of tumor-specific impulse fields through the cells and cell organelles. If the value of the membrane extension (particularly in the tangential direction) exceeds a lethal value, then a necrotic failure occurs. The cell membrane tears and the cell plasma with the cell organelles which are contained therein flow into the surrounding ECM. Malignant cell fragments, malignant protein structures and particularly mitochondrial fragments are expelled. Herein, a tumor-specific maturation of dendritic cells occurs. These present tumor-toxic characteristics to the native T-cells and can lead to a tumor-toxic response of the immune system. Healthy cells survive the tumor-specific impulse propagation without damage. They have an intact actin filament. The stiff cortical actin filament of healthy non-degenerate cells supports the membrane of healthy ones and has a membrane-protective effect.

Given a corresponding embodiment, the invention apart from the tumor-specific impulse shape, also preferably comprises a tumor-specific impulse sequence. The impulse sequence is determined by the impulse frequency and the number of impulses. Herein, what is significant is the viscoelastic delay behavior of malignant cell structures. Significant extension fields occur in the malignant cells after the occurrence of the first impulse shock. These are more pronounced than in normal cells. The second impulse shock amplifies the already built-up extension fields. Consequently, the extensions are built up further until reaching lethal values and lead to the necrotic destruction. Healthy non-degenerate cells require longer time intervals in order to achieve lethal extensions. Given short impulse sequences, they remain below the critical cell-destroying values and survive the impulse sequences without damage.

In the context of the invention, one can envisage an equally high negative pressure shock following a positive pressure shock, or two positive pressure shocks being able to be delivered, between which a defined delay time (time between the pressure shocks) is adjusted. An optimal impulse shape for the tumor destruction is sought by way of the variation of the delay time. The time, at which the extension fields in the tumor superimpose and thus add until they become lethal to the tumor cells, is sought. Each tumor cell has an individual extension characteristic which is imaged in the individual delay time. Healthy cells survive the tumor-specific impulse propagation without damage. They have an intact actin filament. The stiff cortical actin filament of healthy, non-degenerate cells supports the membrane of healthy cells and has a membrane-protective effect. The stiffness of the cells is primarily defined by the cytoskeleton.

The cytoskeleton consists of a multitude of different protein structures, particularly actin filaments, microtubules, microfilaments and interfilaments.

Herein, actin filaments and the microtubules play an important role. Actin filaments are decisive for the total stiffness of the cells. They support the cell membranes. Concerning most malignant cells, particularly at the cortical inner side of the cell membranes, actin filaments are almost not present at all, are less bundled and cannot fulfil their physiological protective support function of the cell membranes. The tumor cell can be extended more easily and tear due to the lower stiffness.

Given a suitable further development of the invention, one can envisage at least two pressure sound heads or oppositely polarised piezoelements being applied in phased-array technology for producing the impulse sequences and the defined delay time between the impulses.

In the context of the invention, one can further envisage metastases of the skeleton, of the trunk, of the liver, of the head, of the neck as well as tumor recurrences, operated and irradiated (unresolved) recurrences being able to be treated.

Concluding, the invention relates to patient-individual destructive impulse shapes and impulse sequences in the tumor region. For determining lethal impulse shapes and impulse sequences, tumor cells are preferably taken from the patient, from the primary tumor or metastasis cells which circulate in the blood circulation. The physical characteristics of the removed cells can be determined in subsequent AFM measurements and be integrated into FEM simulation models. The results of the simulation analyses are patient-individual impulse shapes and impulse sequences which can be applied in the tumor region after validating experiments. For this, preferably in a second step patient-individual MRT data is integrated into a stable, predefined FEM model and the non-linear pressure propagation in the tumor region is determined. The parameters and positions of the TMI treatment applications which are of relevance to the invention and which can be applied for the sequential scanning of the complete tumor region result from the results of the FEM analyses.

Further features and embodiment examples result from the subsequent explanation of embodiment examples by way of the drawing.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
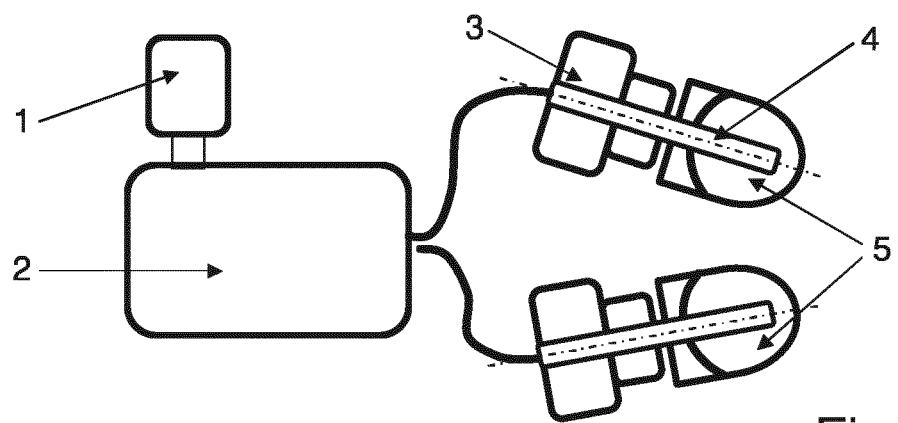
FIG. 1 is a schematic view showing the construction of a TMI device.

Referring to the drawings, the possible embodiment of a TMI device is schematically represented in FIG. 1. The device comprises a central control unit or central processing unit (CPU) 1, a TMI impulse generator 2, a positioning mechanisms 3, diagnostic units 4 and treatment applicators 5 with a transmission medium.

The treatment applicators 5 are provided with suitable positioning mechanisms 3 and a diagnostic unit 4. The alignment and positioning of the treatment applicators 5 is effected with the positioning mechanisms 3. The treatment applicators 5 are connected to the skin of a tissue region which is to be treated, via a transmission medium (not shown) in the form of a coupling membrane or gel layer. The control of the impulse generators 2 is configured such that tumor-destructive impulse shapes and impulse sequences are applied. The treatment applicators 5 which are flexibly integrated in a treatment dome or a treatment ring (cf. FIG. 12) in a regular manner are aligned onto the tumor region, and are subjected to tumor-destructive impulse sequences via the control unit 1. Tumor nodes are treated via several treatment applicators 5 which are focused upon the nodes. The tissue which surrounds the tumor, with tumor-protective fibroblasts (TAFS) which are activated by the tumor are scanned by way of lethal impulse shapes which are applied in a pointwise manner and are treated in a concomitant or time-staggered manner.

The application of TMI treatment applicators 5 with a point-like focus is advantageous. Herein, the positioning mechanisms 3 are activated with the help of the diagnostic unit 4 such that the point-like focus of the TMI device scans the complete tumor region. A pulsed control of the TMI treatment applicators 5 is advantageous in order to avoid an overheating in the focus region.

Figure 2:
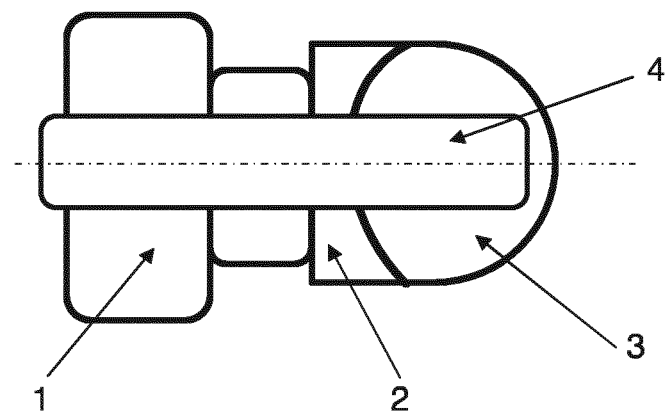
FIG. 2 shows a schematic representation of a TMI treatment applicator.
Figure 3:
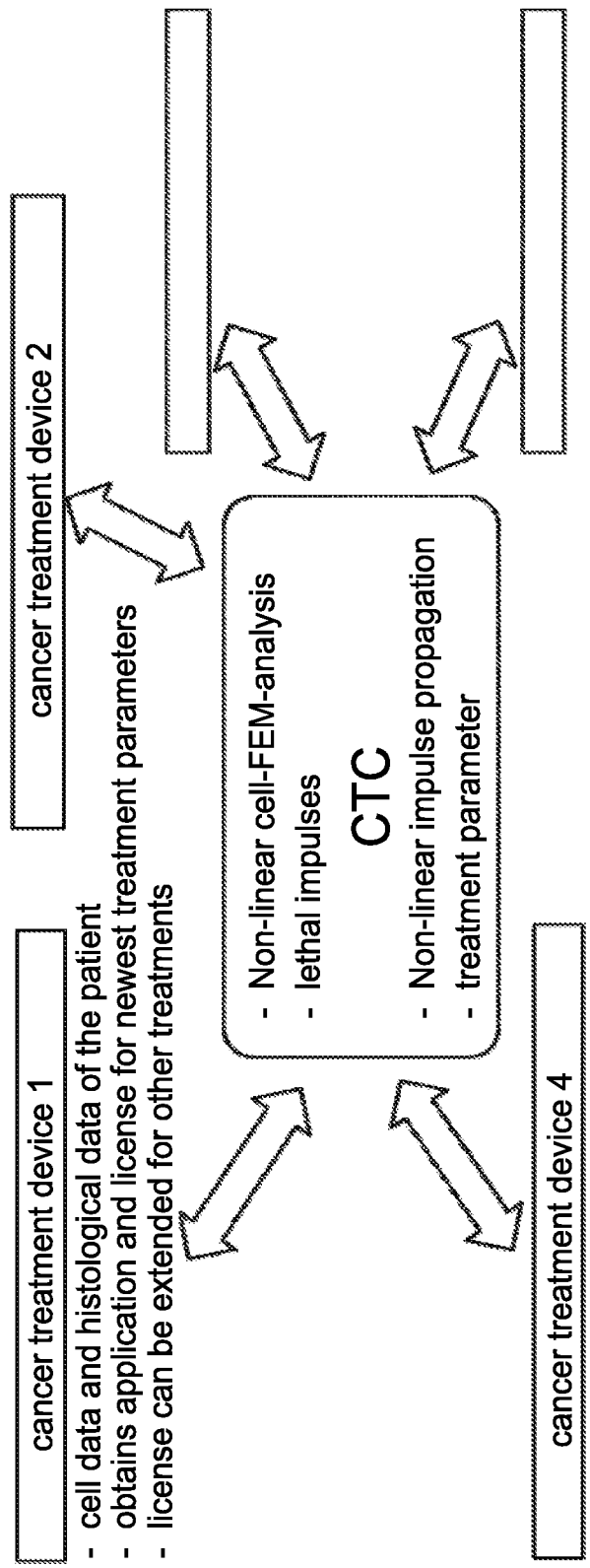
FIG. 3 is a view showing the construction of a TMI cancer treatment center (CTC)
Figure 4:
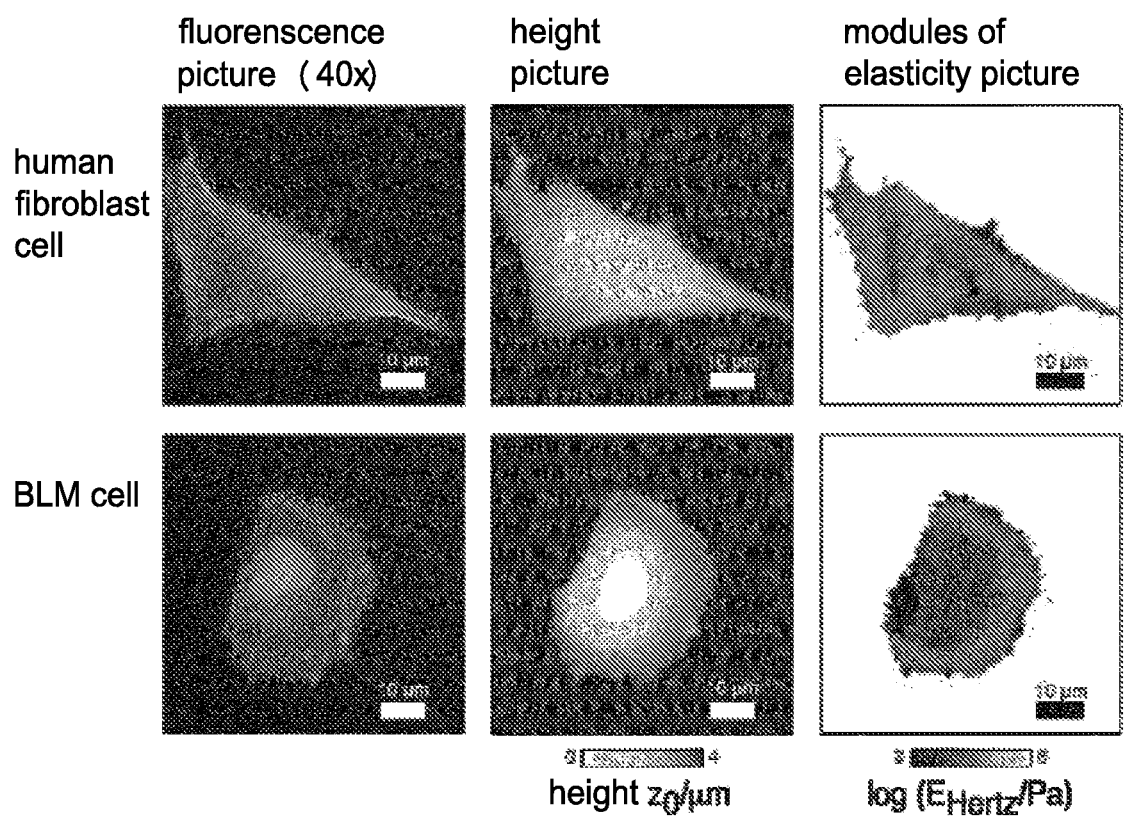
FIG. 4 is a view showing the AFT determining of the patient-individual cell data.
Figure 4:
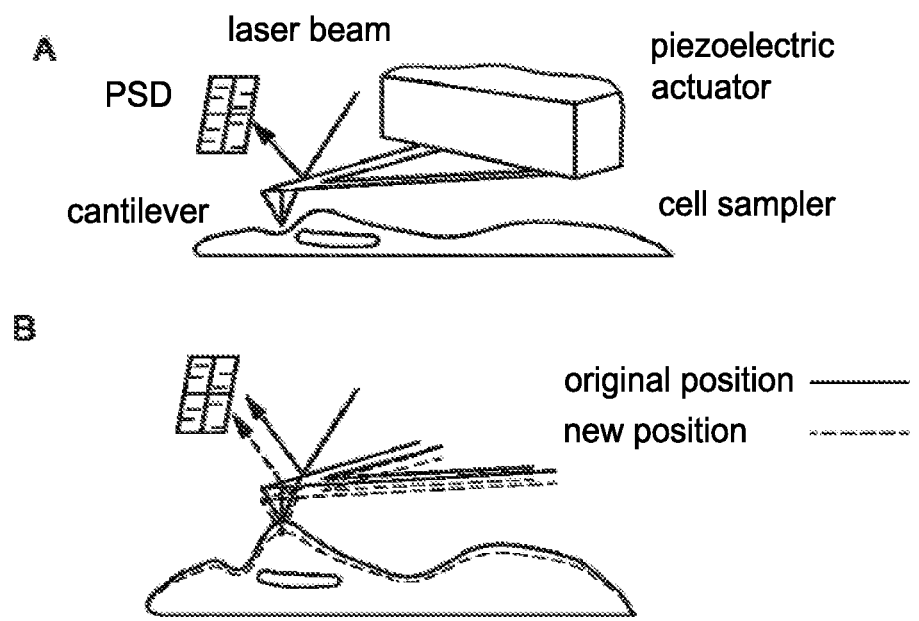

A TMI treatment applicator is schematically represented by way of example in FIG. 2. It comprises a positioning mechanism 1, a focused, pulsed treatment applicator 2, a transmission medium 3 and a low frequency (20-30 kHz) treatment applicator.

Figure 5:
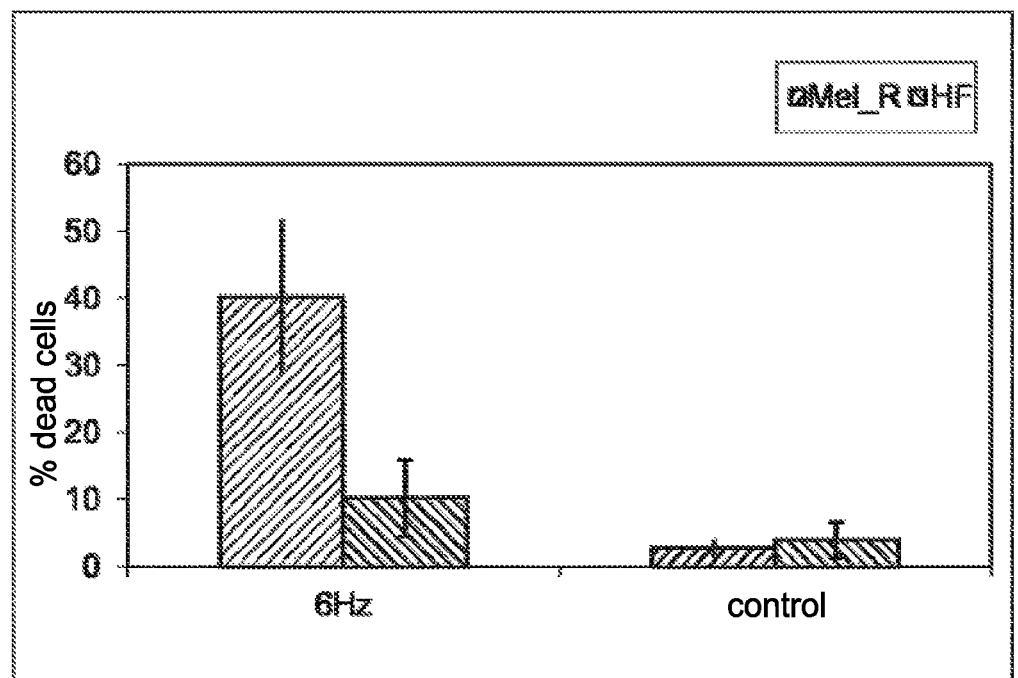
FIG. 5 is a graph showing a validating comparison of TMI-treated melanoma cells.

A diagram showing cells which are lethally damaged by the TMI treatment is shown in FIG. 5. What are shown are FM-human melanocytes, human fibroblasts and W3734 vermurafenib-resistant melanoma cells.

Figure 6:
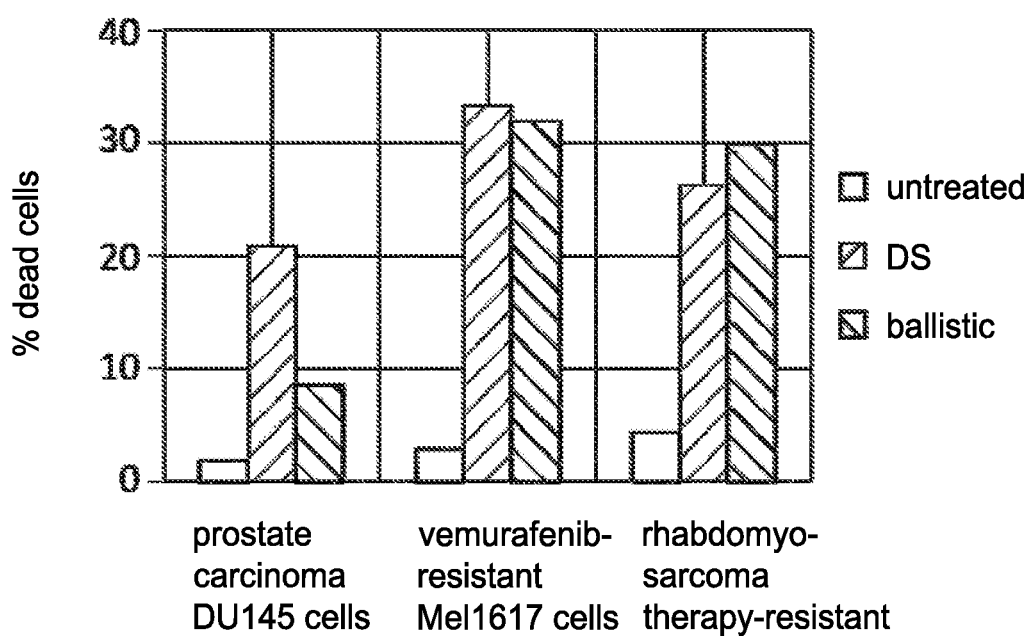
FIG. 6 is a graph showing a validating comparison of TMI treated prostate carcinoma cells, vemurafenib-resistant melanoma cells and rhabdomio sarcoma cells.
Figure 7:
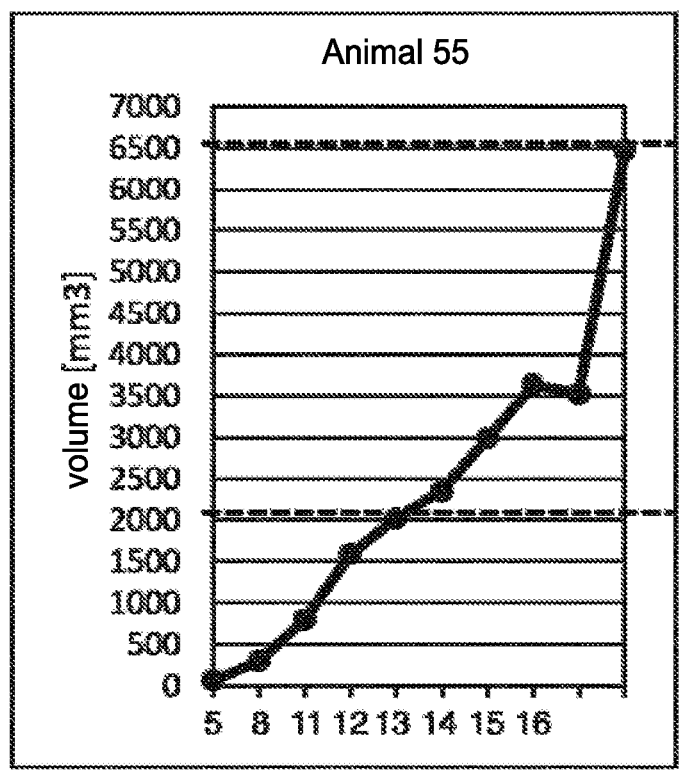
FIG. 7 is a view showing a validating TMI treatment of tumor-carrying, immune-competent animals (hares) and a comparative comparison of the results (untreated animal with aggressively growing tumor)
Figure 8:
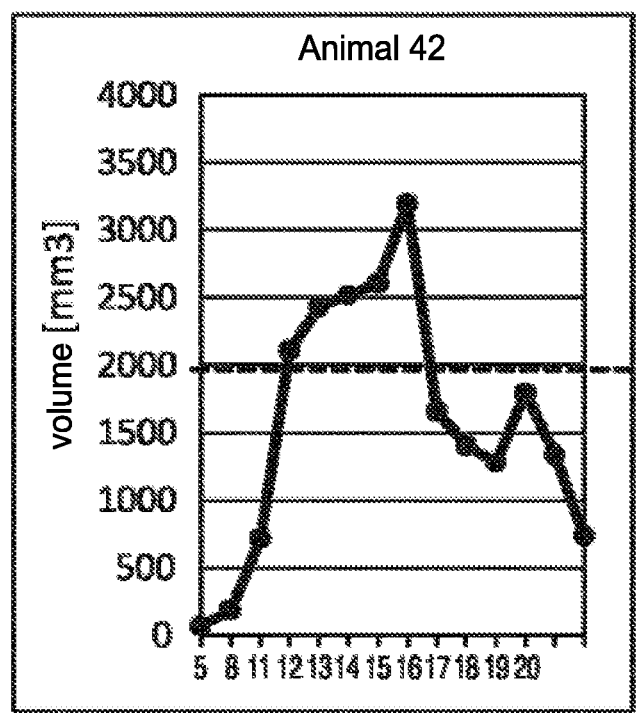
FIG. 8 is a view showing a validating TMI treatment of tumor-carrying, immunocompetent animals (hares) and a comparative comparison of the results (tumor regression after three TMI treatments)
Figure 9:
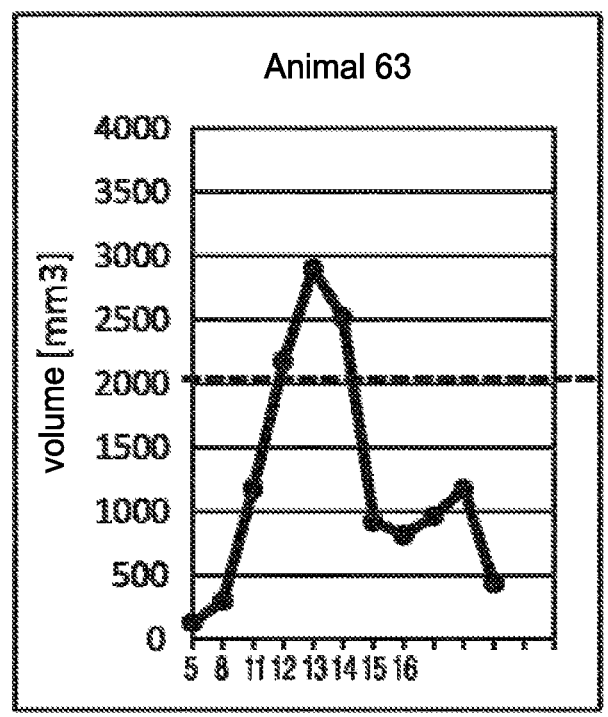
FIG. 9 is a view showing a validating TMI treatment of tumor-carrying, immune-competent animals (hares) and a comparative comparison of the results (tumor regression after three TMI treatments in combination with Nivolumab)
Figure 10:
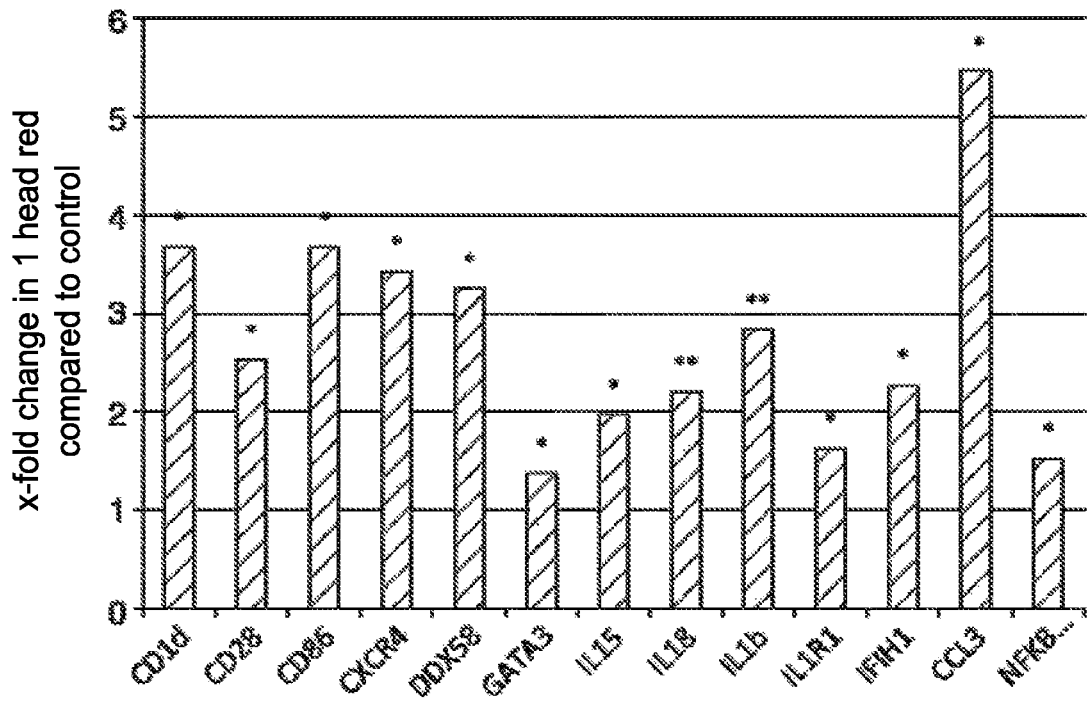
FIG. 10 is a view showing a validating TMI treatment of tumor-carrying, immune-competent animals (hares) and a comparative comparison of the results (increase of the immune-markers after three TMI treatments)
Figure 10:
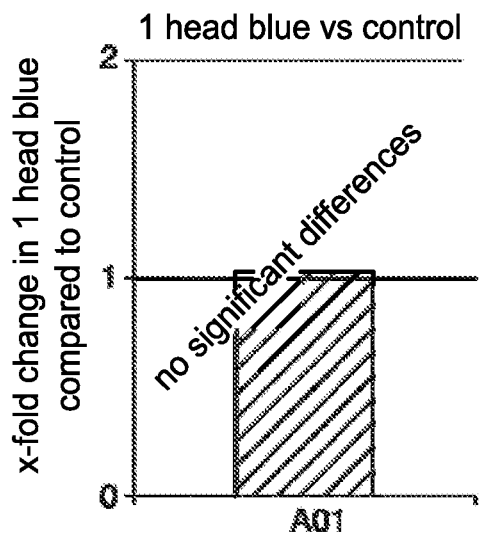
Figure 11:
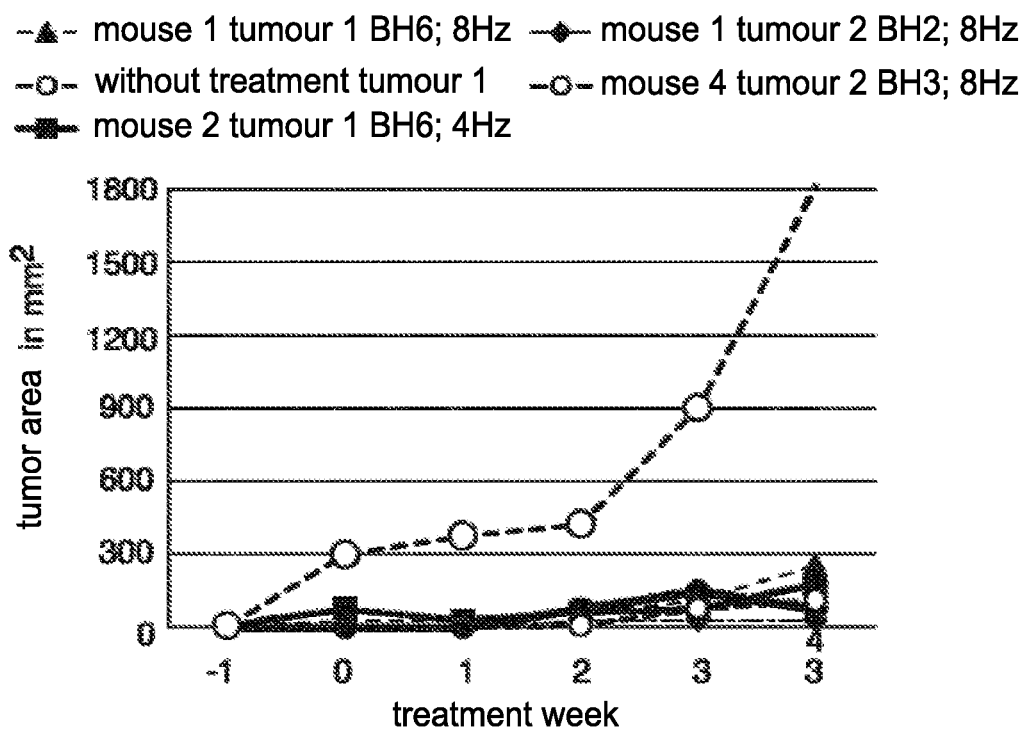
FIG. 11 is a graph showing a validating TMI treatment of tumor-carrying immune-competent animals (mice) and a comparative comparison of the results (tumor progression with the untreated animals and the TMI-treated animals)

A diagram showing lethally damaged cells caused by TMI treatment is shown in FIG. 6. What is shown are DU145 prostate carcinoma cells, ME1617 vemurafenib-resistant melanoma cells and ZF rabdomyo-sarcoma cells.

Healthy cells survive the TMI treatment without any damage, as can be derived from FIG. 5 to FIG. 9.

Figure 12:
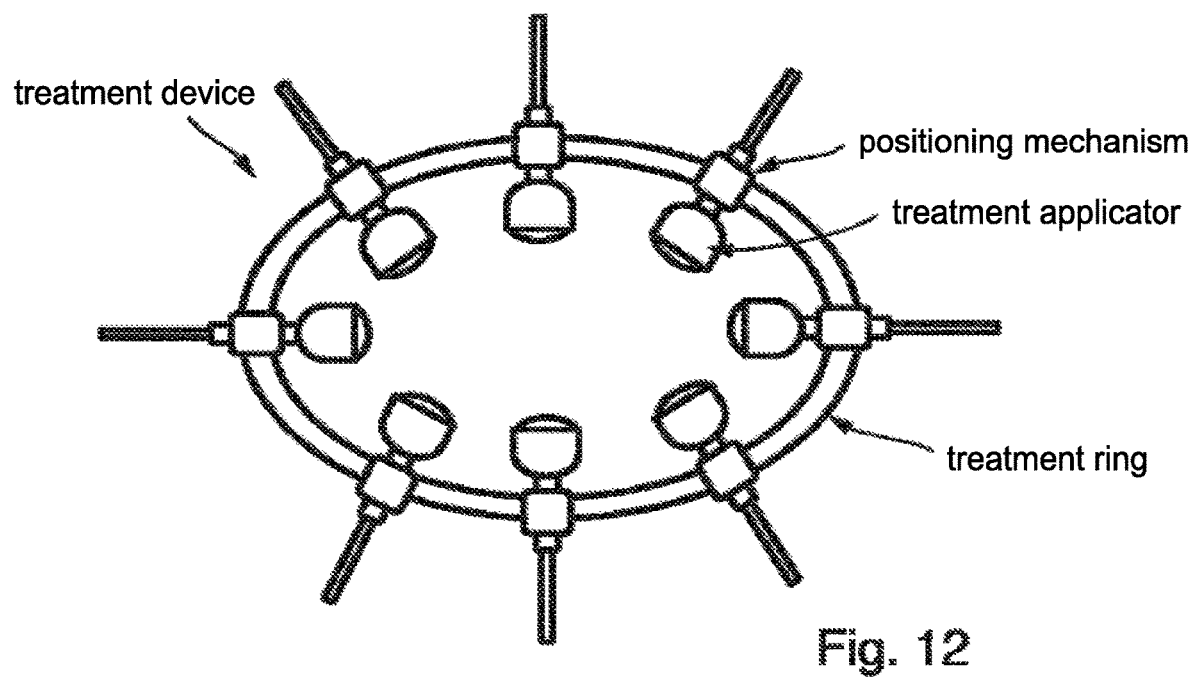
FIG. 12 is a schematic view showing a TMI device for the treatment of brain metastases.

FIG. 12 shows a TMI device (or TMI treatment device) BV for the selective, extracorporeal treatment of therapy-resistant cerebral metastases and primary cerebral tumor disease with the help of mechanical impulse fields. The TMI device BV comprises a treatment ring BR which is fastened to the head of a patient and on which a number of treatment applicators BA are arranged. The reference numeral PM indicates a positioning mechanism which belongs to each treatment applicator BA.

The TMI device BV also comprises at least one therapy-accompanying diagnostic unit (not represented) and a positioning mechanism or several positioning mechanism. The treatment applicators BA are adjustably arranged thereon and transmit the mechanical impulse fields onto the skull via the respective coupling membrane (not shown) which is typically provided with a transmission gel. The various treatment applicators BA are herein attached to a treatment ring BR and in the shown example are directed onto a tumor region. Targeted mechanical impulse fields which ensure a destruction of the tumor can be produced at the location of the tumor by way of the targeted control of the individual treatment applicators BA.

Figure 13:
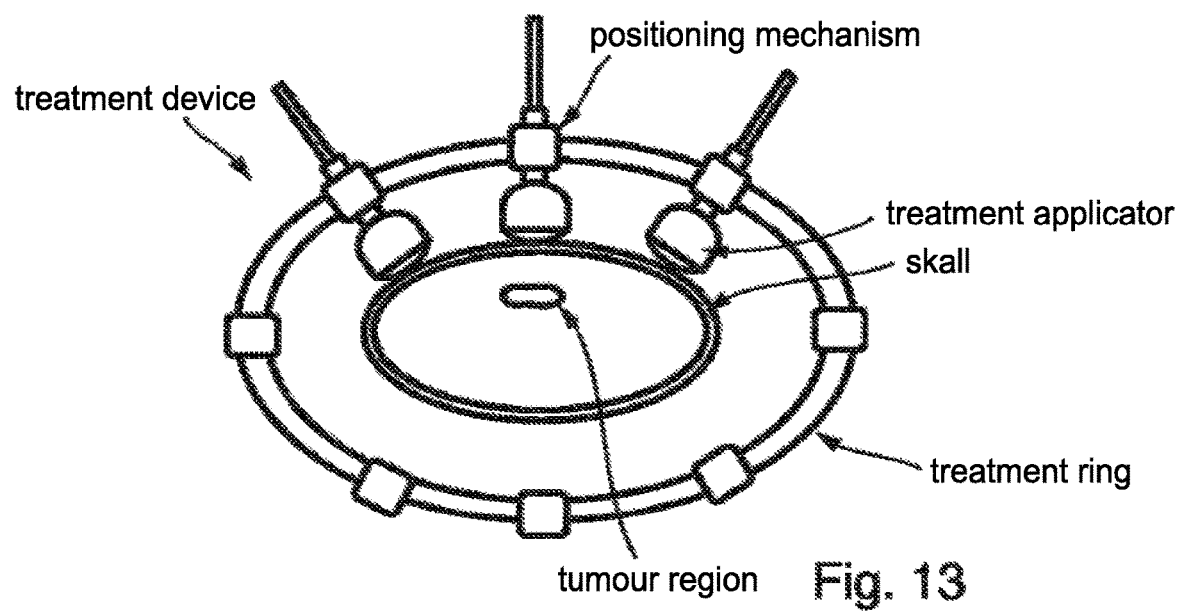
FIG. 13 is a schematic view showing a TMI device for the treatment of brain metastases with a unilateral arrangement of treatment applicators.

A variant of the TMI treatment device of FIG. 12 is shown in FIG. 13. Furthermore, the skull SK of a patient and a tumor region TA which is located therein are represented. The treatment device BV according to FIG. 13 differs from that of FIG. 12 in that the treatment ring BR merely surrounds a part of the skull SK. This treatment ring, as is shown in FIG. 13, can be configured in the shape of a semicircle wherein other variants are not to be ruled out. A unilateral arrangement of the TMI treatment applicators BA is shown in FIG. 13. Herein, the treatment ring BR is configured in a completely peripheral manner, as is shown in FIG. 13, wherein however only one side of the treatment device BV is provided with treatment applicators BA.

As is shown in FIGS. 12 and 13, typically more than three treatment applicators are arranged extracorporeally with the help of positioning mechanism and are positioned on the skullcap via a coupling gel, for the extracorporeal, selective TMI treatment of central metastases and primary cerebral tumor disease. The skull absorbs between 50 and 80% of the energy of the impulse fields. The remaining impulse energy is so low that healthy brain regions are not damaged. The superimposed and modulated impulse fields and impulse sequences are sufficient to effect lethal damage for primary cerebral tumor cells and cerebral metastasis cells. What is particularly relevant here are the focused treatment of the tumor regions and the subsequent treatment of possible micro-metastases by way of a uniform distribution of impulse fields in the complete healthy brain mass. The impulse shape, the impulse sequence and the modulation of the impulse fields are herein selected accordingly.

Figure 14:
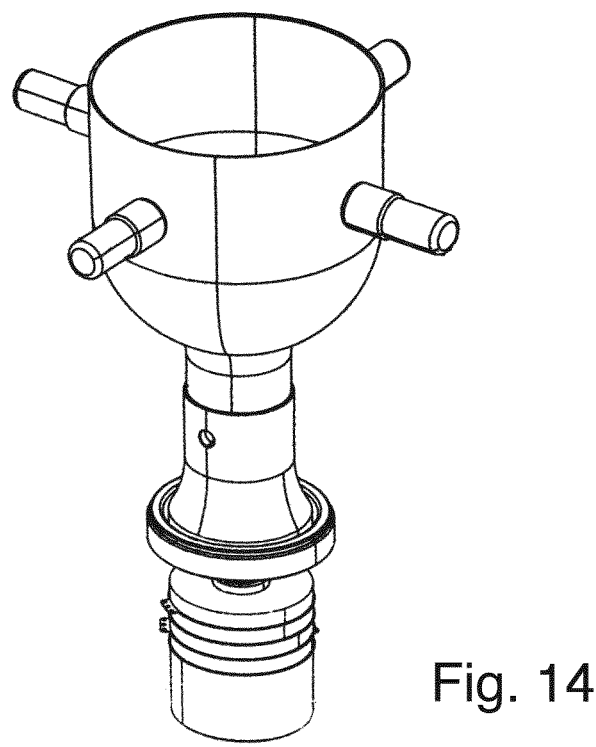
FIG. 14 is a perspective view showing a TMI device for the treatment of a mammary carcinoma.

A special TMI device according to the invention, for the extracorporeal, selective treatment of the mammary carcinoma is described hereinafter. Such a treatment device can be constructed schematically similarly as is shown in FIG. 14 and FIG. 15.

The TMI device in FIG. 14 again comprises impulse generators, a control device, several treatment applicators and imaging therapy-accompanying components.

The treatment applicators of the TMI device for the treatment of the mammary carcinoma induce tumor-destructive impulse shapes and impulse sequences in the tumor region. Concerning the focused applicators, a pronounced pressure increase occurs in the focus. The tissue is compressed. A non-liner increase of the sonic speed, a steepening of the pressure flanks and a classic pressure shock with highly tumor-destructive characteristics occurs. Pressure shocks can be induced via capacitive discharges in piezoelectric or electromagnetic applicators or be applied via focused, pulsed sine oscillations (p-HIFU) in the tumor region. Such an arrangement is particularly advantageous for the selective, non-thermal treatment of the mammary carcinoma since our own computations and validating tumor trials have led to the recognition that tumor-destructive impulses have a maximal tumor-destructive effect when the tumor region is heated to 39-41° C. before the actual treatment. Pulses which heat the tumor region to 39-41° C., preferably about 40° C. are applied before the actual treatment.

Figure 15:
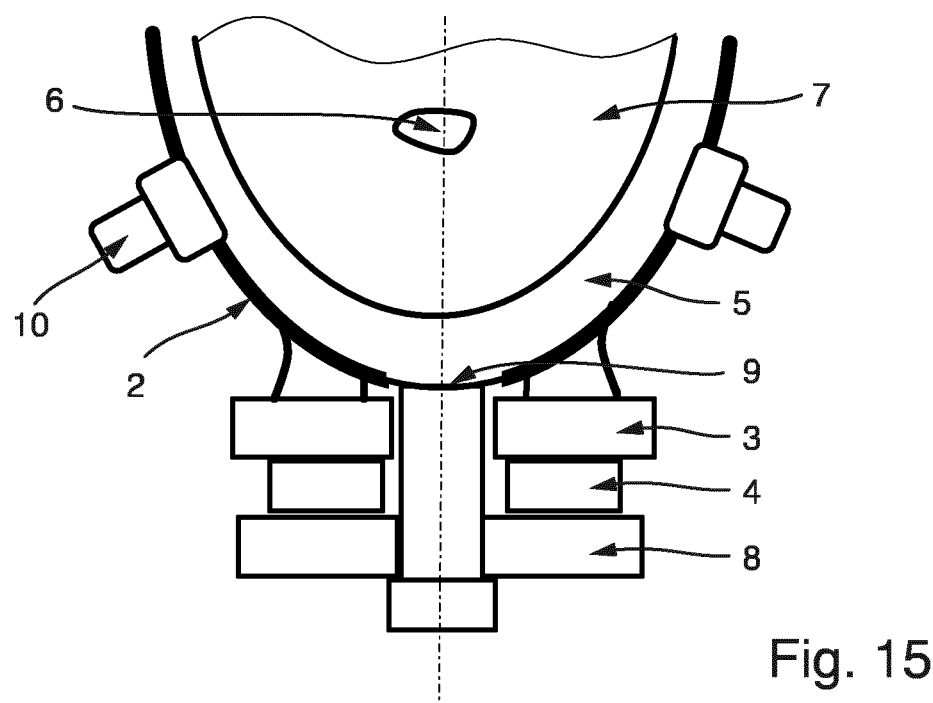
FIG. 15 is a sectional view showing a TMI device for the treatment of the mammary carcinoma.

The device in FIG. 15 can comprise several different impulse generators. Herein, it can be useful to apply piezoelectric, ballistic or electromagnetic impulse generators or a combination of the mentioned impulse generators. With the extracorporeal treatment of tumor regions of the mammary carcinoma, the arrangements of at least two electromagnetic or piezoelectric treatment applicators are preferred for organ-specific reasons. These treatment applicators can be operated synchronously or asynchronously.

The focused treatment of the tumor regions and the subsequent treatment of possible micro-metastases by the uniform distribution of the impulse fields in the complete region are of relevance to the invention concerning the TMI device for the treatment of the mammary carcinoma. Affected lymph nodes are not excised, but treated by way of TMI.

The TMI device for the treatment of the mammary carcinoma according to FIG. 14 is configured as a vacuum treatment bell and comprises a threaded plunger 1, the bell wall 2, an ultrasound lower part 3, piezo-discs 4, a transmission medium 5, the ultrasound threaded disc 8, a membrane 9 and applicators with positioning mechanism 10. The reference numeral 6 indicates the tumor region, 7 the breast tissue.

The construction of a vacuum treatment bell for the destruction of micro-metastases in breast tissue 7 (cf. FIG. 15) and which is represented in FIGS. 14 and 15 comprises pressure shock applicators 10 which are integrated in the wall 2. The breast is sucked into the treatment bell which is configured in a hollow-walled manner. The pressure shock applicators 10 are aligned onto the tumor region 6 with the help of an imaging diagnostic unit (not shown). Vacuum oscillations are applied in the complete breast tissue 7 via the ultrasound converter, in a concomitant or time-shifted manner. The selectively acting oscillations (preferably 14-40 kHz) are not focused and affect the complete breast tissue 7. The frequency of the tumor-destructive oscillations is determined in prior FEM analyses. Healthy cells of the breast tissue 7 survive the treatment without any damage.

Figure 16:
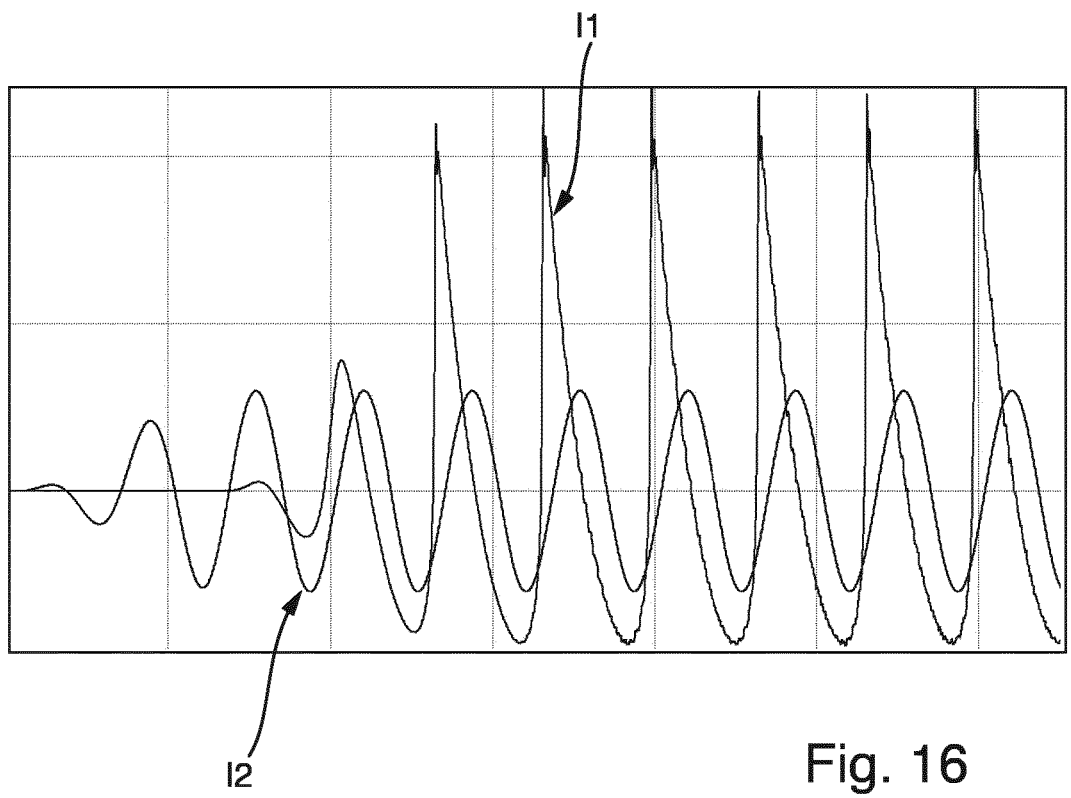
FIG. 16 is a graph showing steepened impulse flanks in the tumor region and continuous sinusoidal oscillations, with a TMI device for the treatment of the mammary carcinoma.

FIG. 16 shows steepened impulse flanks in the tumor region (curve with reference numeral 11) and continuous sine oscillations (curve with reference numeral 12), these having been produced by way of a TMI device for the treatment of the mammary carcinoma, in particular according to FIG. 14 or 15.

Figure 17:
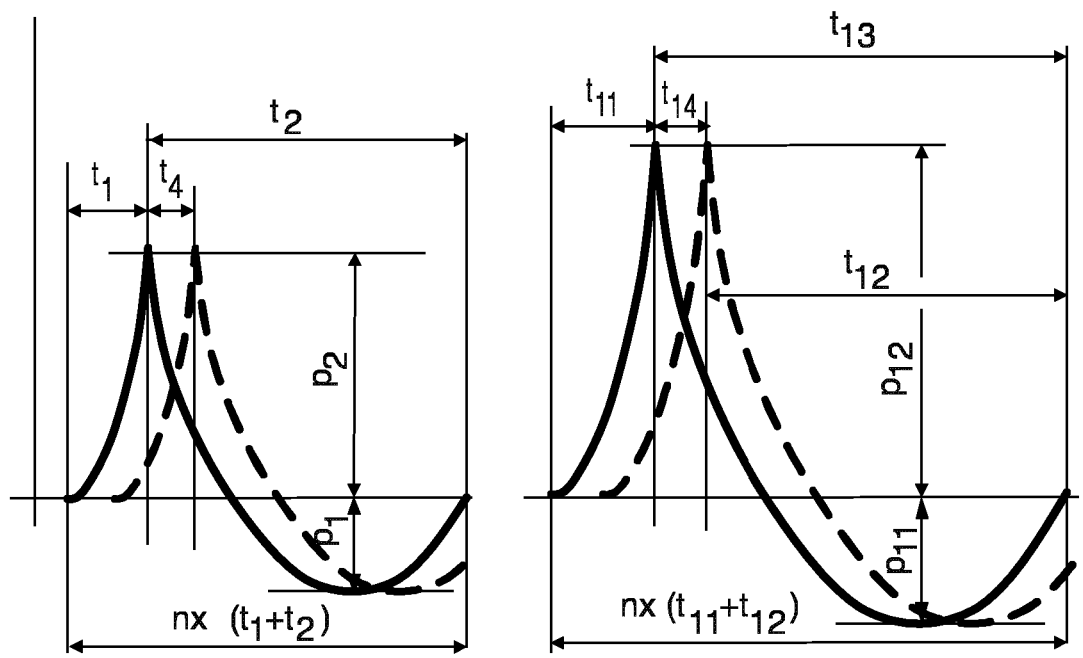
FIG. 17 is a graph showing lethal impulse flanks in the tumor region, said impulse flanks having been produced by a TMI device.

Tumor-destructive impulse shapes and impulse sequences with sequentially applied impulses in the low intensity range (−10 MPA-60 MPA) and the high intensity range (−20 MPA-120 MPA), as are producible or are produced with a device according to the invention, are represented by way of example in FIG. 17. The control of the device is herein configured such that a sequence of low-energetic impulse shapes ($t_1$-$t_2$) for the destruction of cellular bonding proteins is applied before the actual treatment ($t_{10}$-$t_{11}$). The pretreatment is necessary for the necrotic destruction of malignant tumor cells which are embedded in the extracellular matrix.

Figure 18:
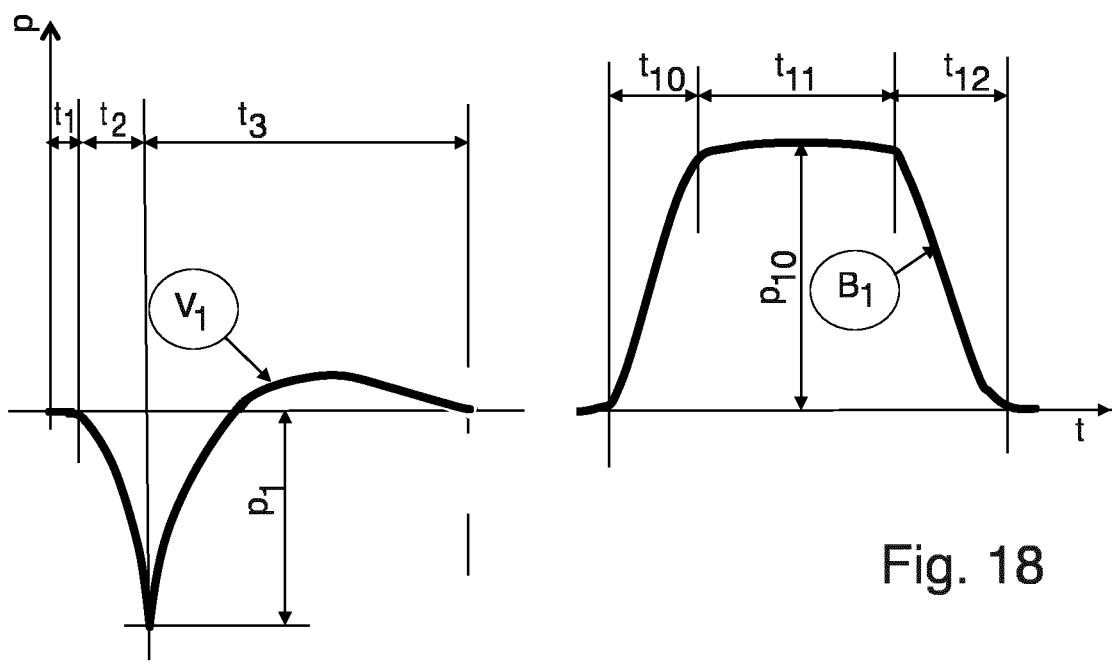
FIG. 18 is a graph showing lethal impulse flanks in the tumor region, said impulse flanks having been produced with a TMI device.

Combined impulse sequences of pressure shock impulse shapes (V1) and ballistic impulse shapes (B1) with sequentially applied, inverted impulses (−0.20 MPA-10.0 MPA) and ballistic impulses (0.0 MPA-40.0 MPA) are represented in FIG. 18. The represented impulse sequence is of relevance to the treatment of therapy-resistant rabdomyo-sarcoma diseases.

Figure 19:
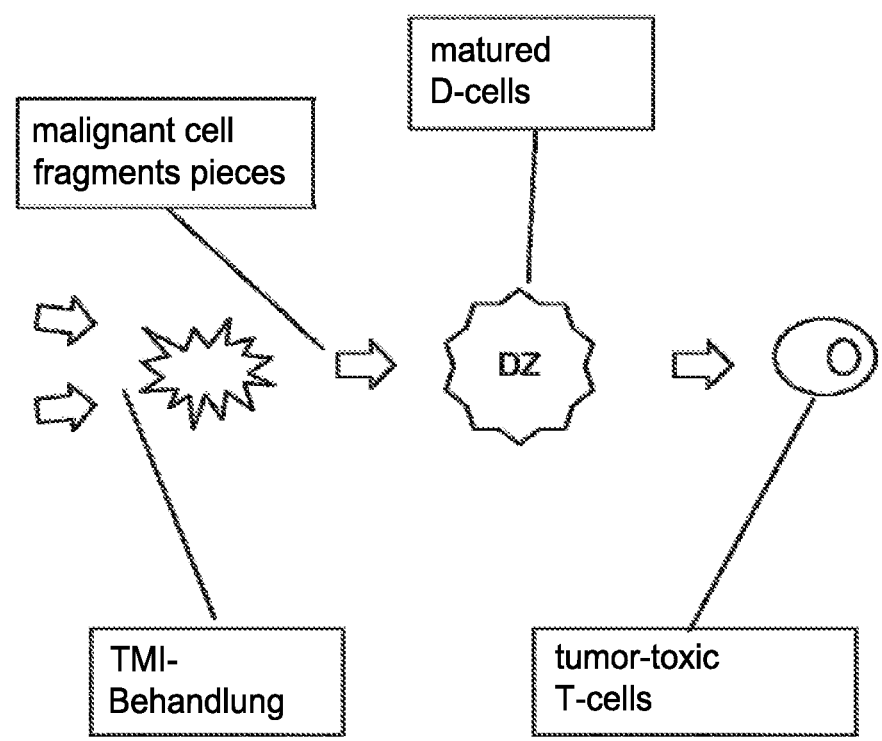
FIG. 19 is a schematic view showing the effect of TMI treatment and response of the immune system.

According to FIG. 19, malignant cell fragments arise due to the TMI treatment and lead to a maturation of dendritic cells and the induction of tumor-toxic characteristics in T-cells of the immune system.

Figure 20:
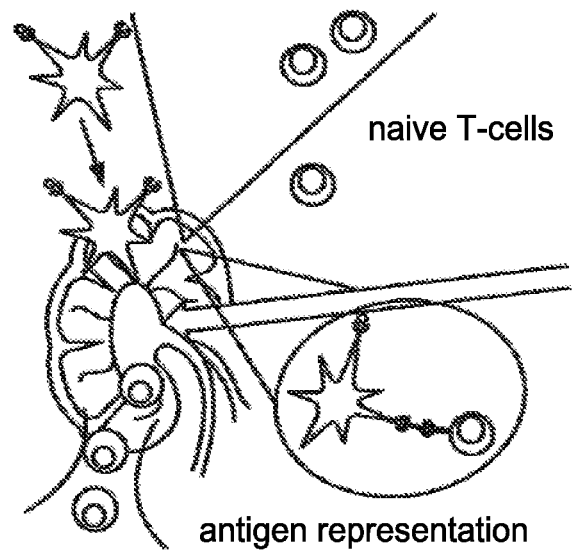
FIG. 20 shows TMI treatment of affected lymph nodes and response of the immune system in combination with PD1 immunomodulators.
Figure 20:
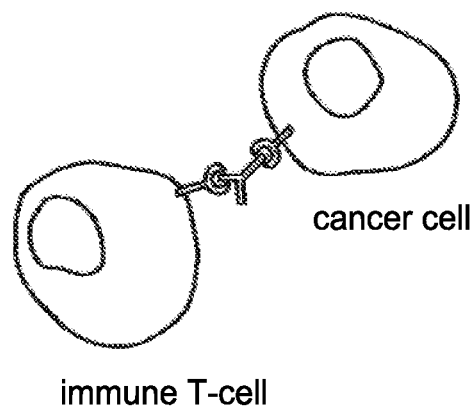

According to FIG. 20, metastasis cells, dendritic cells as well as T-cells of the immune system are located in the affected lymph node. The targeted TMI treatment of affected lymph nodes can lead to a large number of tumor-toxic T-cells. Tumor-protective binding locations of the numerous, newly arisen tumor-toxic T-cells are blocked by way of the simultaneous or time-staggered dosage of PD1 immune modulators, and a systematic tumor-destructive effect unfolds.

While specific embodiments of the invention have been shown and described in detail to illustrate the application of the principles of the invention, it will be understood that the invention may be embodied otherwise without departing from such principles.

The invention claimed is:

1. A device for the treatment of malignant diseases, the device comprising impulse means for generating tumor-destructive mechanical impulses, with cell-biologically optimized, optimally destructive and a tumor-selective, patient-individual impulse shape and/or sequences, said impulse shape and/or impulse sequences resulting from a mechanical, more viscoelastic characteristics of the tumor cells and from an extracellular matrix (ECM) which is intratumoral or encompasses the tumor, and the impulse means comprises at least two shockwave generators and a control unit, the shockwave generators are successively activated or activatable by the control unit to generate shockwave impulses such that respective pressure maxima of the shockwave impulses are successive in a temporal interval which is smaller than an impulse duration of the shockwave impulses such that a time interval between successive ones of the pressure maxima is shorter than the impulse duration and an impulse pressure of one said shockwave impulse has not returned to an initial value before a next said shockwave impulse is generated.

2. A device according to claim 1, wherein the impulse means is configured to apply a cell-biologically optimized, optimally destructive and tumor-selective pressure shock impulse sequence.

3. A device according to claim 1, wherein the impulse means further comprises control means configured to adjust a cell-biologically optimized, optimally destructive and tumor-selective delay time between the impulses wherein the impulse means is adjustable as to the delay time between the impulses.

4. A device according to claim 1 wherein the impulse means is adjustable to provide a widening of a target volume which is subjected to the impulses, into healthy tissue for the destruction of tumor-active fibroblasts.

5. A device according to claim 1, wherein the impulse means comprises at least one pressure sound head and the control unit for activating the pressure sound head for producing tumor-destructive mechanical impulses or impulse sequences.

6. A device according to claim 5, further comprising a positioning mechanism for positioning the at least one pressure sound head relative to a target volume which is subjected to the impulses.

7. A device according to claim 5, wherein the impulse means is configured such that the at least one pressure sound head is positioned or is positionable and is modulated or modulatable with regard to an impulse delivery thereof such that tumor-destructive shear forces arise in the target volume.

8. A device according to claim 1, wherein the impulse means comprises at least two pressure sound heads and oppositely polarised piezoelements in phased-array technology with corresponding positioning mechanisms, for generating tumor-selective impulse shapes and impulse sequences.

9. A device according to claim 1, wherein the impulse means comprises for treatment of the mammary carcinoma or of brain metastases, at least three or more pressure sound heads with corresponding positioning mechanism whereby the pressure sound heads are positioned or positionable and with regard to impulse delivery thereby, are modulated or modulatable, in a manner such that tumor-destructive shear forces arise in a tumor region.

10. A device according to claim 8, wherein the positioning mechanisms are controlled or are controllable such that a focus region is firstly directed onto a tumor edge and this scanned, wherein the impulse flanks comprise high-frequency components of about 1 MHZ to 10 MHz.

11. A device according to claim 6, wherein the positioning mechanism is controlled such that a focus region is directed onto the target volume and scans this, wherein impulse flanks comprise patient-individual low-frequency shares, at about 0.1 MHz-3 MHz.

12. A device according to claim 1, wherein the target volume is heated to about 39° C. to 41° C. by way of suitable impulses or impulse sequences.

13. A device according to claim 1, wherein the impulse means comprises at least one ballistic and/or at least one electrohydraulic or piezoelectric shockwave generator or corresponding treatment applicators for generating positive shockwave impulses.

14. A device according to claim 1, wherein the impulse means comprises at least one ballistic shockwave generator for producing second shockwave impulses.

15. A device according to claim 1, further comprising at least one diagnostic unit for continuous monitoring of a treatment success, for monitoring an ultrasound echo picture of a tumor region, a number of circulating tumor cells in the blood and/or immune parameters.

16. A method for operation and control of a tumor-destructive mechanical impulse device, comprising impulse means for generating tumor-destructive mechanical impulses, with cell-biologically optimized, optimally destructive and a tumor-selective, patient-individual impulse shape and/or sequences, said impulse shape and/or impulse sequences resulting from mechanical, more viscoelastic characteristics of the tumor cells and from an extracellular matrix (ECM) which is intratumoral or encompasses the tumor, the method comprising determining an optimal impulse shape and/or impulse sequence and/or further operating parameters in a cell trial on cells which are taken from the patient or based on a tissue trial or taken from a data bank of cell trials and tissue trials, before an application of the device, wherein physical characteristics of the removed cells are determined via atomic force microscopy (AFM) measurements and are integrated into finite element modelling (FEM) simulation models, and the tumor-destructive impulse shapes and impulse sequences result from the FEM simulations that are based on the AFM analysis.

17. A method according to claim 16, wherein the operating parameters are determined in a patient-individual manner with the help of physical characteristics of cells taken from a patient and on the basis of MRT/CT data of the patient.

18. A method according to claim 16, wherein lethal impulse shapes and impulse sequences are determined with the help of patient-individual numerical simulation models and are experimentally validated.

19. A method according to one of the claim 16, wherein the operation of the tumor-destructive mechanical impulse treatment is effected via a central treatment center and de-central treatment facilities.

20. A method according to claim 16, wherein the tumor-destructive mechanical impulse device is aligned onto tumor-affected lymph nodes, in order to treat these individually.

21. A method according to claim 16, wherein the tumor-destructive mechanical impulse device is used simultaneously with an application of immune modulators.

22. The method according to claim 16, wherein the FEM simulation models yield said tumor-destructive impulse shape and/or impulse sequences.

23. A device for treatment of malignant diseases, the device comprising
- impulse means for generating tumor-destructive mechanical impulses, with cell-biologically optimized, optimally destructive and a tumor-selective, patient-individual impulse shape and/or sequences, said impulse shape and/or impulse sequences resulting from a mechanical, more viscoelastic characteristics of the tumor cells and from the extracellular matrix (ECM) which is intratumoral or encompasses the tumor,
- wherein the tumor-destructive impulse shapes and/or sequences include sequentially applied ones of the impulses having a same pressure maxima in a low intensity range of 10 MPA-60 MPA followed by sequentially applied ones of the impulses having a same pressure maxima in a high intensity range of 20 MPA-120 MPA, and the impulse means is configured such that a sequence of the impulses in the low intensity range for destruction of cellular bonding proteins is applied before an actual treatment such that a time interval between successive ones of pressure maxima is shorter than an impulse duration.

\* \* \* \* \*